(12) United States Patent
Weihermueller

(10) Patent No.: US 8,512,268 B2
(45) Date of Patent: Aug. 20, 2013

(54) ORTHOPEDIC AUXILIARY AID COMPRISING AN INTRODUCEABLE FUNCTIONAL ELEMENT

(75) Inventor: Stefan Weihermueller, Bayreuth (DE)

(73) Assignee: Medi GmbH & Co. KG, Bayreuth (DE)

( * ) Notice: Subject to any disclaimer, the term of this patent is extended or adjusted under 35 U.S.C. 154(b) by 113 days.

(21) Appl. No.: 12/988,683

(22) PCT Filed: Apr. 21, 2009

(86) PCT No.: PCT/DE2009/000511
§ 371 (c)(1),
(2), (4) Date: Oct. 20, 2010

(87) PCT Pub. No.: WO2009/129780
PCT Pub. Date: Oct. 29, 2009

(65) Prior Publication Data
US 2011/0040222 A1    Feb. 17, 2011

(30) Foreign Application Priority Data

Apr. 21, 2008    (DE) ............... 20 2008 005 533 U

(51) Int. Cl.
*A61F 5/00*    (2006.01)
(52) U.S. Cl.
USPC ............ 602/20; 602/23; 602/60; 602/63

(58) Field of Classification Search
USPC .............. 602/5, 20–27, 60–63; 128/856, 128/878–879
See application file for complete search history.

(56) References Cited

U.S. PATENT DOCUMENTS

| 3,602,914 A * | 9/1971 | Castello .............. 2/90 |
| 4,870,956 A | 10/1989 | Fatool |
| 5,421,811 A | 6/1995 | More |
| 5,720,042 A * | 2/1998 | Wilkinson .......... 2/69 |
| 6,029,277 A | 2/2000 | Picchione, II |
| 2005/0197608 A1 | 9/2005 | Taylor |
| 2005/0273030 A1* | 12/2005 | Koby et al. .......... 602/60 |
| 2009/0005718 A1* | 1/2009 | Lightbourne ........ 602/75 |

FOREIGN PATENT DOCUMENTS
EP    0 496 071 A1    7/1992

* cited by examiner

*Primary Examiner* — Michael A. Brown
(74) *Attorney, Agent, or Firm* — Lucas & Mercanti, LLP

(57) ABSTRACT

The invention relates to an orthopedic auxiliary aid such as a bandage, orthesis, splint, support, compressive clothing and/or knitted item or similar for the therapy or support of corresponding body parts, comprising a functional element have additional therapeutic effects. Said orthopedic auxiliary aid is a compressive knitted part that comprises at least one receiving device for the additional functional element and at least one opening that is embedded in the knitted item allowing access to the receiving device, said opening does not negatively modify the compression properties of the auxiliary aid.

8 Claims, 2 Drawing Sheets

ORTHOPEDIC AUXILIARY AID COMPRISING AN INTRODUCEABLE FUNCTIONAL ELEMENT

CROSS-REFERENCE TO RELATED APPLICATIONS

This application is a 371 of PCT/DE2009/000511 filed Apr. 21, 2009, which in turn claims the priority of DE 20 2008 005 533.4 filed Apr. 21, 2008, the priority of both applications is hereby claimed and both applications are incorporated by reference herein.

The present invention relates to an orthopedic aid, a bandage, orthosis, splint, support, a compressive clothing item or knitted item or similar, for the therapy or support of corresponding parts of the body, in particular to such aids designed as a knitted item.

Orthopedic aids have proven their worth over the years and are used not only in the therapeutic treatment of symptoms, including those following surgery, but also as bracing, protecting or supporting means for corresponding parts of the body.

In particular, bandages for various parts of the body, e.g. knee joints, elbow joints or wrists, are worn in cases of inflammation of the joints and/or after injury, or are worn for preventive purposes in various activities, e.g. sport, in order to take care of the corresponding joints, to support them or to protect them from renewed injury or excessive loads.

It has been found that such aids have to satisfy very different and changing requirements for different uses and for different parts of the body.

For instance, if it is desired to support a person's knee, for example, via the outer aspect of the leg, this may be disadvantageous in other cases or at another time for recovering mobility in the same person, for example at an advanced stage of the healing process, when the restoration of the muscles is delayed by the bandage providing too much support.

In principle, various bandages are available that are also tailored to such changing requirements, for example knee bandages with or without integrated pads for the knee-cap or with sewn-in lateral stiffening elements, for example in order to limit the flexion of the knee joint or to reduce lateral loads. According to the same principle, bandages for the wrist are also known which have corresponding stiffening elements, by means of which, for example, twisting or hyperflexion of the wrist is avoided.

Said stiffening elements are integrated into the bandages or other aids at suitable places and are connected to the bandage. For this reason, one person often requires various bandages in order to cover different degrees of the supporting action, for example a more strongly supporting knee bandage following an operation, after which a lesser supporting action is needed in order to permit better restoration of the muscles.

Bandages or aids would therefore be desirable that have an adjustable or modifiable supporting action and an additional action, for example an additional therapeutic or medical function.

The object of the present invention is to make available an orthopedic aid which meets the changing requirements in respect of a variable supporting action and an additional therapeutic or medical function.

This object is achieved by the features disclosed herein. Developments and advantageous embodiments of the invention are covered in the following.

According to the invention, an orthopedic aid such as a bandage, orthosis, splint, support, clothing item or knitted item or similar, for the therapy or support of corresponding parts of the body, with a functional element with additional therapeutic action, wherein the orthopedic aid is a compressive knitted item that has at least one receiving device for the additional functional element, and at least one opening introduced into the knitted item and providing access to the receiving device, which opening does not negatively modify the compression properties of the aid.

The receiving part is preferably a pocket for the additional functional element, which pocket is arranged, for example, on the outer face of the bandage or splint, for example, is arranged over the opening in the orthopedic aid and is sewn on, welded on or glued on there. Access to this applied receiving device or pocket is made possible, for example from the inside, through the opening in the knitted item, wherein the additional functional element is introduced through this opening into the pocket and can easily be removed again or replaced. In this way, for example, different supporting functional elements can easily be introduced alternately and can perform different applications for a treatment in which the body part concerned is supported to a greater or lesser degree by a corresponding functional element.

Depending on the requirements, these means can have different degrees of hardness or stiffness, in order thereby to perform different degrees of a supporting or protective function. It is possible in this way, for example, to considerably immobilize a knee joint directly after an operation by wearing such a bandage with a very stiff addition and then, after a certain period of healing, to reduce this immobilization by replacing the insert with a less stiff material in order to support the recovery of mobility. In this way, it is possible to support the development of the muscles in the joint, which would take place much more slowly if a bandage with a very stiff insert were to be worn constantly.

The bandages or the like according to the invention preferably have a non-fraying opening or hole in the knitted item, and a pocket or receiving device for the additional means is formed on one side of the bandage and is adapted in shape and size to the means to be used. The opening is preferably designed as a slit in the transverse direction of the knitted item and is introduced in the knitting process, as a result of which the edge of the opening is directly non-fraying, without additional strengthening or any required taking-in of the edge. By means of this knitting technique in the formation of the opening, an optimal opening for the additional functional element is obtained, and the knitted item thereby maintains its compressive properties, for example in respect of its periphery in the case of a bandage for the wrist, which would not be the case with an opening in the longitudinal direction, since the opening would interrupt the compression profile. Moreover, fraying of an opening that was produced only by cutting out or punching out, for example, would, during the course of use, negatively influence the compressive properties of such an orthopedic aid designed as a knitted item. In principle, however, formation of the opening in the longitudinal direction is alternatively also possible according to the invention, particularly at locations where the compressive action or the defined profile of the compression action does not have high priority.

A receiving pocket is sewn on, glued on or otherwise permanently secured on one side of the bandage and can be reached via the opening formed in the bandage.

The additional functional part can now be pushed through the opening into the pocket. The opening and the receiving pocket are arranged relative to each other in such a way that the pocket extends beyond the opening on both sides, and a functional element is first pushed through the opening in the direction of the longer side of the pocket, and the remaining part of the functional part can be pushed fully into the pocket by slight stretching of the bandage. After it has been inserted, the functional part therefore extends across the opening and cannot therefore accidentally slide out while the bandage is being worn.

The functional part, for example a stiffening rod made of plastic, metal, glass, carbon fiber or other materials, can easily be taken out through the opening, preferably on the inner face of the bandage, and can be replaced by another one or completely removed.

In addition to the use of functional parts for supporting the various parts of the body, it is also possible to use functional elements, for example with thermal or other actions, e.g. a medical action. These can be used, for example, as rods or gel packs with a cooling or heating action, as a result of which inflammations or swelling in the joints can be treated. Corresponding inserts with active substances which are dispensed near the joint and have a medical or therapeutic action can thus be used without complication. According to another variant, it is also possible to use functional parts with additional stimulating elements, for example massage knobs or electrically stimulating elements. These too can be removed and/or replaced at any time.

The invention is described in more detail below with reference to the examples in the drawings, in which.

Figure 1:
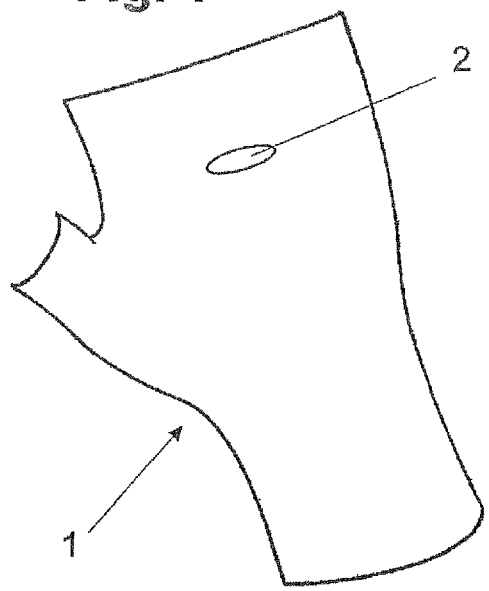
FIG. 1 shows a front view of a wrist bandage with hole.
Figure 2:
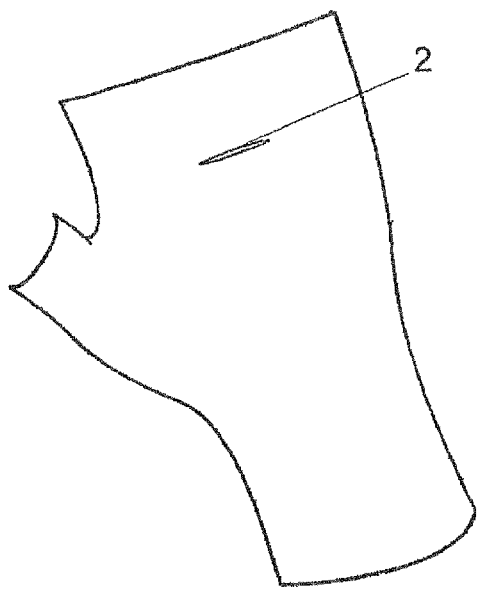
FIG. 2 shows a front view of a wrist bandage with opening slit.
Figure 3:
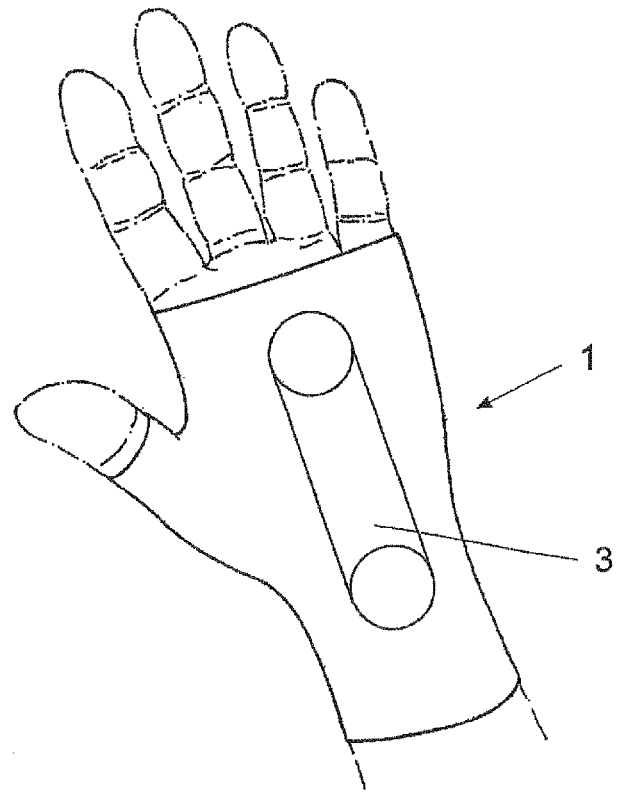
FIG. 3 shows a front view of a wrist bandage, worn with receiving pocket.

In FIG. 1, a bandage 1 according to the invention for a wrist is shown which has the described opening 2, the latter being shown slightly widened here for the purpose of illustration. The unwidened opening in the bandage is shown in FIG. 2. A pocket 3, as shown in FIG. 3, is fitted over this passage 2, which pocket 3 is preferably applied on the outer face of the orthopedic aid.

The pocket is optically depicted with limiting circles at the top and bottom, which represents purely a design variant and does not represent any openings. Now, as is shown here by way of example, an additional therapeutic or medical means can be pushed into this pocket 3 through the opening 2, from the direction of the inner face of the wrist bandage into the pocket 3.

Small stiff rods are preferably inserted here, e.g. in order to prevent the flexion movement of the hand and to keep the latter immobilized for the required time.

After the injury has healed, the small stiff rod pushed into the pocket 3 can be removed or can be replaced by a suitably softer one in order to modify the degree of immobilization.

Figure 4:
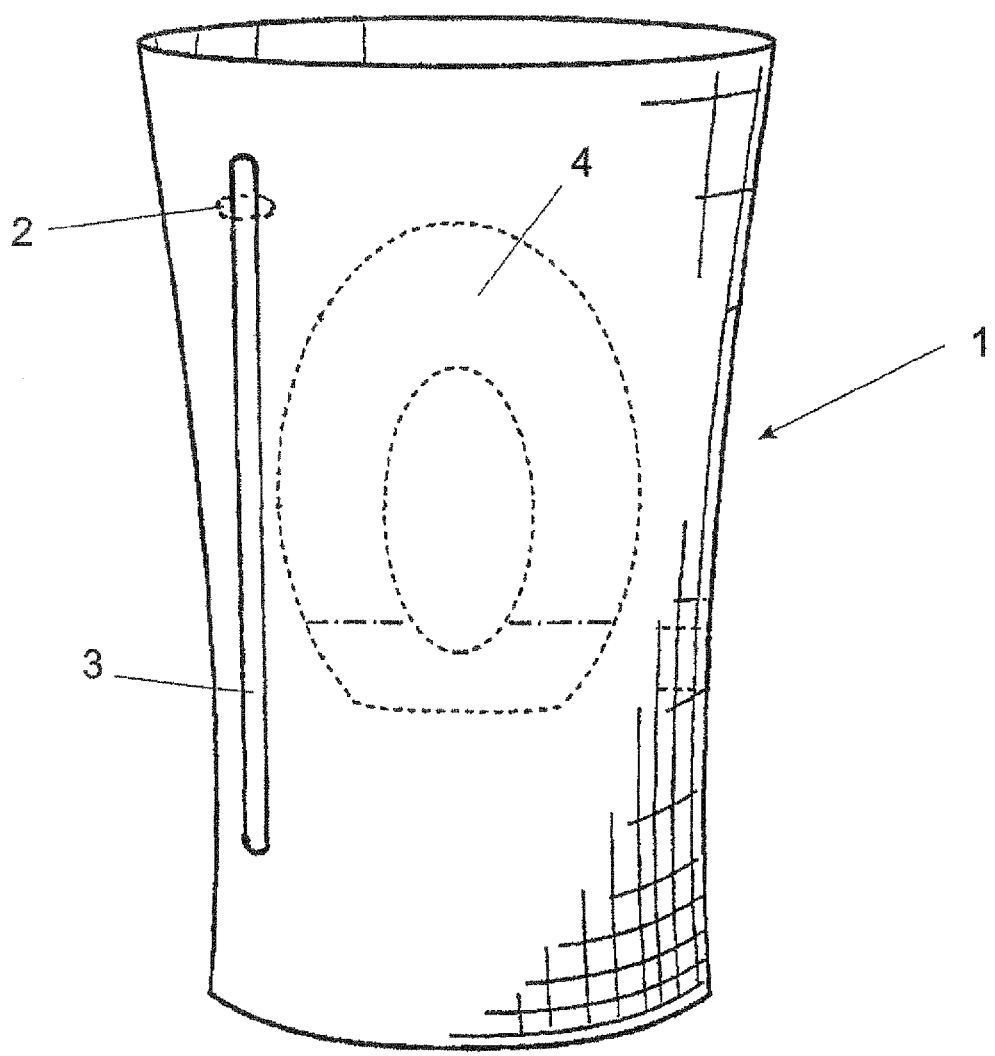
FIG. 4 shows a perspective view of a knee bandage.

FIG. 4 shows a knee bandage 1, which has a pad 4 already introduced for the knee-cap and which is also designed with a receiving pocket 3 applied on the outer face of the bandage.

Here too, a rod can be pushed through the opening 2 and into the receiving pocket 3 from the direction of the inner face of the bandage. Since the pocket 3 and the rod that is to be pushed in protrude upward beyond the opening 2, the rod is pushed completely into the pocket by slight stretching of the bandage 1 and therefore extends in the pocket across the opening 2, as a result of which it is fixed in the pocket.

With preferred embodiments of the invention having been described in relation to the attached drawings, it should be noted that the invention is not limited to these specific embodiments and uses, and that various changes and modifications thereto can be made by a person skilled in the art without departing from the scope of the invention as defined in the attached claims.

The invention claimed is:

1. An orthopedic aid comprising:
a compressive knitted sleeve made by a knitting process, for the therapy or support of corresponding parts of the body;
a functional element with additional therapeutic action;
at least one receiving pocket applied on one side of the knitted sleeve the at least one receiving pocket housing the additional functional element; and
at least one opening in the knitted sleeve, the opening is a slit formed during the knitting process, extends in a transverse direction of knit such that an edge of the slit is non-fraying and non-tearing without additional strengthening or any required taking-in of the edge,
the slit providing access to the receiving pocket through the knitted sleeve, and,
the slit does not negatively modify the compression properties of the knitted sleeve.

2. The orthopedic aid of claim 1, wherein functional elements with additional therapeutic action can be alternately introduced into the receiving pocket.

3. The orthopedic aid of claim 1, wherein the receiving pocket is sewn on, welded on or glued on to the knitted sleeve.

4. The orthopedic aid of claim 1, wherein the functional element with additional therapeutic action has an action that influences temperature.

5. The orthopedic aid of claim 1, wherein the functional element with additional therapeutic action has a medical action.

6. The orthopedic aid of claim 1, wherein the functional element with additional therapeutic action is designed as a solid body that exerts an action.

7. The orthopedic aid of claim 1, wherein the functional element with additional therapeutic action is designed as a gel or at least partially elastic pad that exerts an action.

8. The orthopedic aid of claim 1, wherein the functional element with additional therapeutic action is designed as an elastic shaped body that exerts an action.

* * * * *

UNITED STATES PATENT AND TRADEMARK OFFICE
CERTIFICATE OF CORRECTION

PATENT NO.      : 8,512,268 B2  Page 1 of 1
APPLICATION NO. : 12/988683
DATED           : August 20, 2013
INVENTOR(S)     : Stefan Weihermueller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 71 days.

Signed and Sealed this

Fifteenth Day of September, 2015

Michelle K. Lee
*Director of the United States Patent and Trademark Office*